United States Patent [19]
Takeuchi

[11] Patent Number: 5,311,783
[45] Date of Patent: May 17, 1994

[54] SYSTEM FOR AUTOMATICALLY SHIFTING A MEASURING RANGE OF SURFACE AREA MEASURING DEVICE

[75] Inventor: Minoru Takeuchi, Tokyo, Japan
[73] Assignee: Nikkiso Company Ltd., Tokyo, Japan
[21] Appl. No.: 721,533
[22] PCT Filed: Aug. 31, 1990
[86] PCT No.: PCT/JP90/01112
 § 371 Date: Jul. 13, 1992
 § 102(e) Date: Jul. 13, 1992
[87] PCT Pub. No.: WO91/03724
 PCT Pub. Date: Mar. 21, 1991

[30] Foreign Application Priority Data
Aug. 31, 1989 [JP] Japan .................................. 1-225861

[51] Int. Cl.$^5$ .......................................... G01N 15/08
[52] U.S. Cl. .................................................. 73/865.5
[58] Field of Search ....................... 73/149, 865.5, 866

[56] References Cited
U.S. PATENT DOCUMENTS

| | | |
|---|---|---|
| 2,960,870 | 11/1960 | Nelsen et al. |
| 3,211,006 | 10/1965 | Haley |
| 3,577,076 | 5/1971 | Millham |
| 4,105,967 | 8/1978 | Macemon |

FOREIGN PATENT DOCUMENTS

| | | |
|---|---|---|
| 50-40510 | 5/1974 | Japan |
| 59-65241 | 4/1984 | Japan |
| 59-88616 | 5/1984 | Japan |
| 61-138170 | 12/1984 | Japan |

OTHER PUBLICATIONS

Analytical Instrumentation vol. 15, No. 3, 1986, New York US pp. 241-257; P. Jayaweera et al.: 'High Speed Autoranging of Discontinuous Signals in Data Acquisition Systems Employing Gated Integration' p. 245, line 13–p. 255, line 3.

*Primary Examiner*—Robert Raevis
*Attorney, Agent, or Firm*—Browdy and Neimark

[57] ABSTRACT

The present invention is directed to a system for automatically shifting a measuring range equipped in a surface area measuring device. The system for automatically shifting the measuring range is provided with an output value determining circuit receives a signal for detecting a flow rate of supply gases to be outputted from means for measuring a flow rate of supply gases for detecting an amount of the supply gases to be supplied to a sample cell and a signal for detecting a flow rate of discharge gases of the discharge gases to be outputted from means for measuring a flow rate of the discharge gases for detecting an amount of the discharge gases to be discharged from the sample cell, generates a signal for shifting the gain of an amplifier to a low level during a period for desorption of the gases when a differential signal to be outputted from the amplifier for amplifying the difference between the signal for detecting the flow rate of the supply gases and the signal for detecting the flow rate of the discharge gases, and generates a shift signal for shifting the gain of the amplifier to a high level during a period for desorption when the differential signal to be outputted from the amplifier is smaller than a value set for the gain of the amplifier.

2 Claims, 4 Drawing Sheets

SYSTEM FOR AUTOMATICALLY SHIFTING A MEASURING RANGE OF SURFACE AREA MEASURING DEVICE

TECHNICAL FIELD

The present invention relates to a system for automatically shifting a measuring range of a surface area measuring device and, more particularly, to a system for automatically shifting a measuring range of a surface area measuring device so adapted as to accurately measure an amount of gases adsorbed on a sample in a sample cell in the surface area measuring device.

BACKGROUND TECHNOLOGY

As shown in FIG. 4, a conventional surface area measuring device has a sample cell 2 mounted detachably in a gas passage 1 which has means A for measuring a flow rate of supply gases to be supplied to the sample cell 2 and means B for measuring a flow rate of discharge gases for measuring an amount of gases discharged from the sample cell 2.

A signal G1 for detecting an amount of supply gases generated from the means A for measuring the flow rate of the supply gases and a signal G2 for detecting an amount of discharge gases generated from the means B for measuring the amount of the discharge gases are inputted into an amplifier 3, and the amplifier 3 subtracts the signal G1 for detecting the amount of the supply gases and the signal G2 for detecting the amount of the discharge gases and generates an amplified differential signal G3.

In conventional surface area measuring devices of this kind, the signal G2 for detecting the amount of the discharge gases becomes usually larger than the signal G1 for detecting the amount of the supply gases when the measuring gases are adsorbed on the sample in the sample cell 2 under a cold state, so that the differential signal G3 to be generated from the amplifier 3 is outputted as a negative signal as shown in FIG. 5. The magnitude of the negative differential signal G3 is proportional to the magnitude of the amount of the gases to be adsorbed on the sample. As adsorption of the gases to the sample reaches saturation, the negative differential signal G3 is returned to zero. Thereafter, the cooling of the sample cell 2 is suspended to return the sample cell 2 to ambient temperature. As a result, the gases adsorbed on the sample start desorbing.

As shown in FIG. 5, as the gases are desorbed and the signal G2 for detecting the amount of the discharge gases becomes larger than the signal G1 for detecting the amount of the supply gases, the differential signal G3 becomes an increasing positive signal and the magnitude of the differential signal G3 decreases as the desorption gets finished. And the differential signal G3 is returned to zero as the desorption of the gases has been finished.

In measuring the surface area, the surface area is calculated by integrating the positive differential signals G3 by means of an arithmetic processing unit 4 in a period of time for desorption of the gases and the calculation result is displayed on the display unit 5 and generated.

Such conventional surface area measuring devices of this kind, however, have a switch 6 for shifting gains and the gain of the amplifier 3 is shifted manually. In other words, when the negative differential signal G3 in a period of time for adsorption reaches gain limits of the output of amplifier 3, the gain of the amplifier 3 is shifted manually to a low level, thereby preventing the positive differential signal G3 from reaching the gain limits of the amplifier 3 in a period of time for desorption. If the gain of the amplifier 3 is not shifted, the positive differential signal G3 reaches the gain limit of the amplifier 3 in the period of time for desorption, too, as shown in FIG. 6, and the amount of gases desorbed cannot be accurately calculated by integrating the positive differential signals G3. When the magnitude of the negative differential signal G3' during a period of time for adsorption is too small, the gain of the amplifier 3 should be shifted to a gain of a high level because the surface area cannot accurately be calculated even by integrating minute differential signals G3''.

It is extremely laborious to shift the gains of the amplifier 3 manually and an output should always be monitored during measuring for the surface area. Furthermore, the outcome of measurement may become inaccurate in some cases.

SUMMARY OF THE INVENTION

The present invention has been accomplished under the circumstances as described hereinabove.

More particularly, the object of the present invention is to provide a system for shifting a measuring range of a surface area measuring device so arranged as to be capable of automatically shifting the set gain limit of the amplifier so as to allow the differential signal to reach no set gain limit of the amplifier during a period of time for desorbing gases, in order to accurately calculate the surface area.

In order to achieve the object, the present invention consists of such a surface area measuring device having an amplifier for receiving a signal for detecting a flow rate of supply gases generated from means for measuring an amount of supply gases for detecting the amount of the supply gases to be supplied to a sample cell in a surface area measuring device and a signal for detecting an amount of discharge gases generated from means for measuring a flow rate of discharge gases for detecting the amount of the discharge gases to be discharged from the sample cell and amplifying a difference between the signal for detecting the amount of the supply gases and the signal for detecting the amount of discharge gases, so disposed as to be capable of shifting gains of the amplifier, and arithmetic means for calculating an amount of gases adsorbed on the sample in the sample cell by integrating a signal amplified and generated by the amplifier;

a system for automatically shifting a measuring range of the surface area measuring device characterized by an output value determining circuit for generating a shift signal for setting a gain of the amplifier to a low level during a period of time for desorbing gases when the signal generated by the amplifier reach a set gain of the amplifier and for generating a shift signal for shifting the gain of the amplifier to a high level during the period of time for desorbing gases when the signal generated by the amplifier is smaller than a value set with respect to the set gain of the amplifier.

In accordance with the present invention, the differential signal outputted from the amplifier is outputted to the output value determining circuit during a period of time for adsorbing gases. The output value determining circuit generates a signal for reducing a level of the gain for altering the gain of the amplifier to a low level by comparing the set gain or cutoff value of the amplifier with the differential signal to be inputted, while generating the signal for reducing the level of the gain to the shift switch for shifting the level for the gain, when it is detected that the differential signal reaches zero from a negative value. Further, the output value determining circuit monitors to determine if the differential signal has a constant output during a predetermined period of time. For instance, it monitors to determine if the differential signal exceeds 50% of the gain, and it generates a signal for increasing the level of the gain when the differential signal does not exceed 50% of the gain while it outputs the signal for increasing the level of the gain to a switch for shifting the level of the gain.

The differential signal does not always exceed the gain of the amplifier during a period of time for desorbing gases and the differential signal does not become too small with respect to the gain of the amplifier, so that the surface area can accurately be calculated by integrating the differential signals.

BEST MODES FOR CARRYING OUT THE INVENTION

The present invention will be described more in detail by referring to an example. It is to be noted herein that the present invention is construed as being not limited to the following embodiments and it can appropriately be modified without departing from the scope of the present invention.

Figure 1:
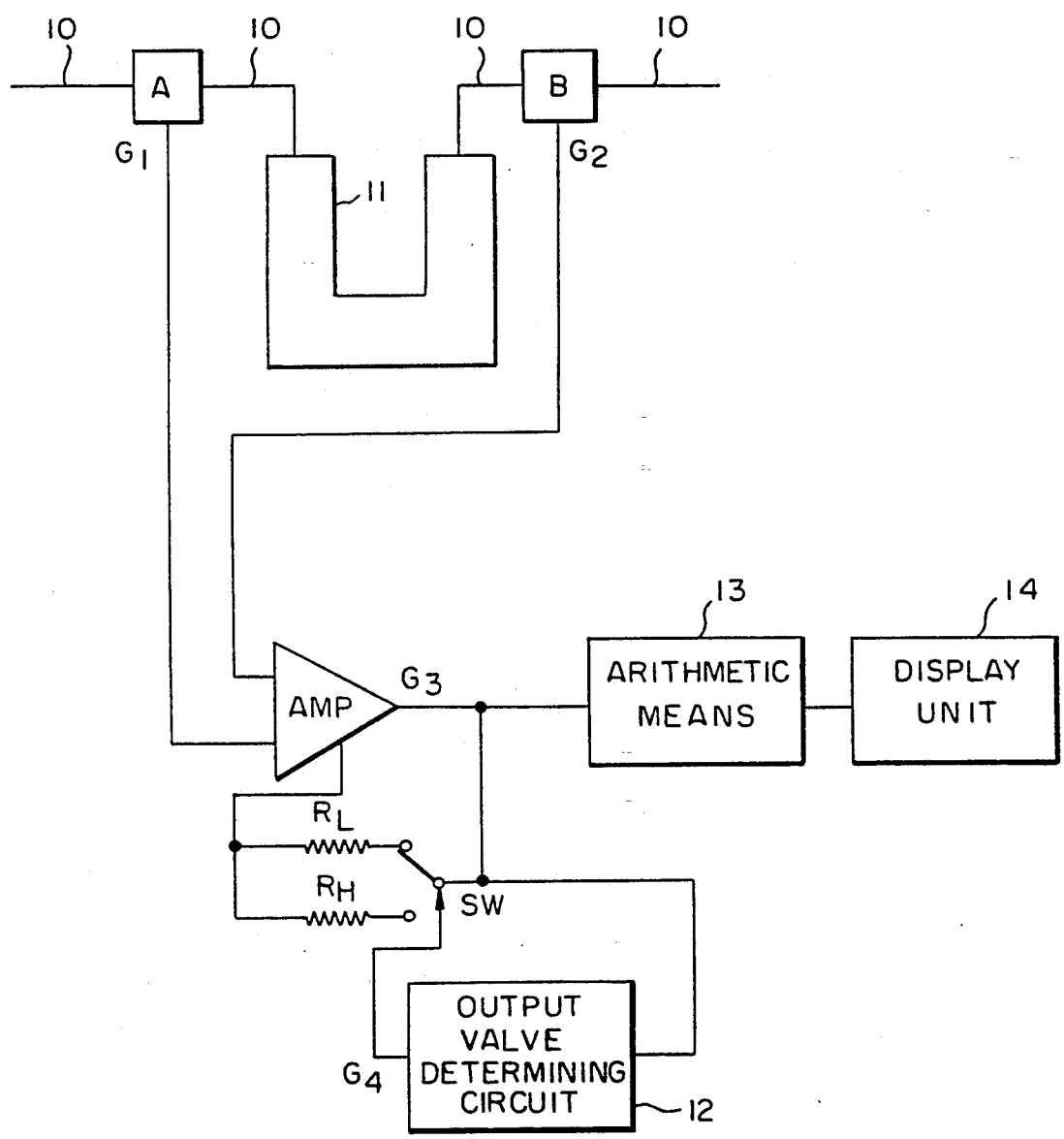
FIG. 1 is a circuit diagram showing an embodiment according to the present invention.

As shown in FIG. 1, the surface area measuring device is such that a sample cell 11 is detachably connected to a passage 10 for measuring gases, means for measuring a flow rate of supply gases, i.e. a first gas flow meter A of thermal conductivity type, which generates the signal G1 for detecting an amount of supply gases by measuring a flow rate of the supply gases to be supplied to the sample cell 11, is disposed in the gas passage 10 for the measuring gases, and means for measuring a flow rate of discharge gases, i.e. a second gas flow meter B of thermal conductivity type, which generates the signal G2 for detecting an amount of discharge gases by measuring a flow rate of the discharge gases to be discharged from the sample cell 11, is disposed in the gas passage 10 for the measuring gases.

This surface area measuring device further has an amplifier AMP, a shift switch SW for shifting gains of the amplifier, an output value determining circuit 12, arithmetic means 13, and a display unit 14.

The amplifier AMP is so arranged as to receive the signal G1 for detecting the amount of supply gases to be generated from the first gas flow meter A of thermal conductivity type and the signal G2 for detecting the amount of discharge gases to be generated from the second gas flow meter B of thermal conductivity type, to subtract one signal from the other signal, and to amplify and generate the differential signal G3.

The aforesaid shift switch SW for shifting the gains of the amplifier AMP is so arranged as to automatically shift the gains of the amplifier AMP between a high level RH and a low level RL in response to a shift signal G4 to be generated from the output value determining circuit 12.

Figure 3:
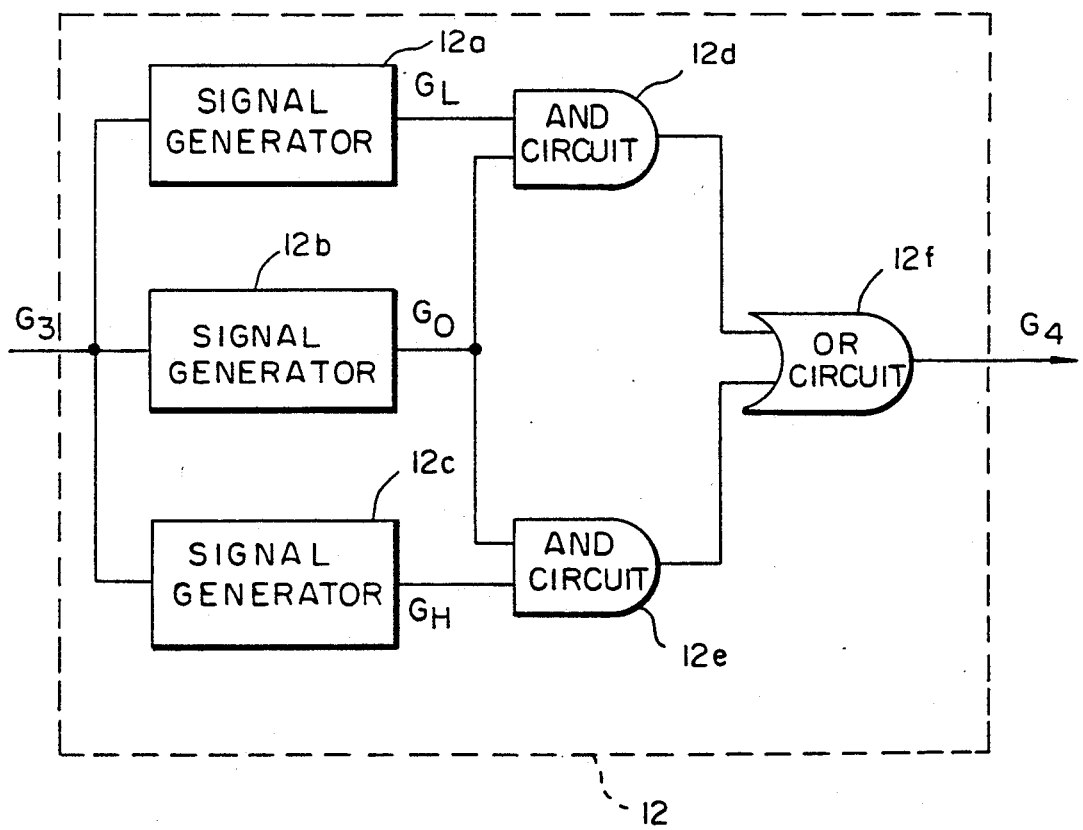
FIG. 3 is a circuit diagram showing an example of the structure of the output value determining circuit in the aforesaid embodiment of the present invention.
Figure 4:
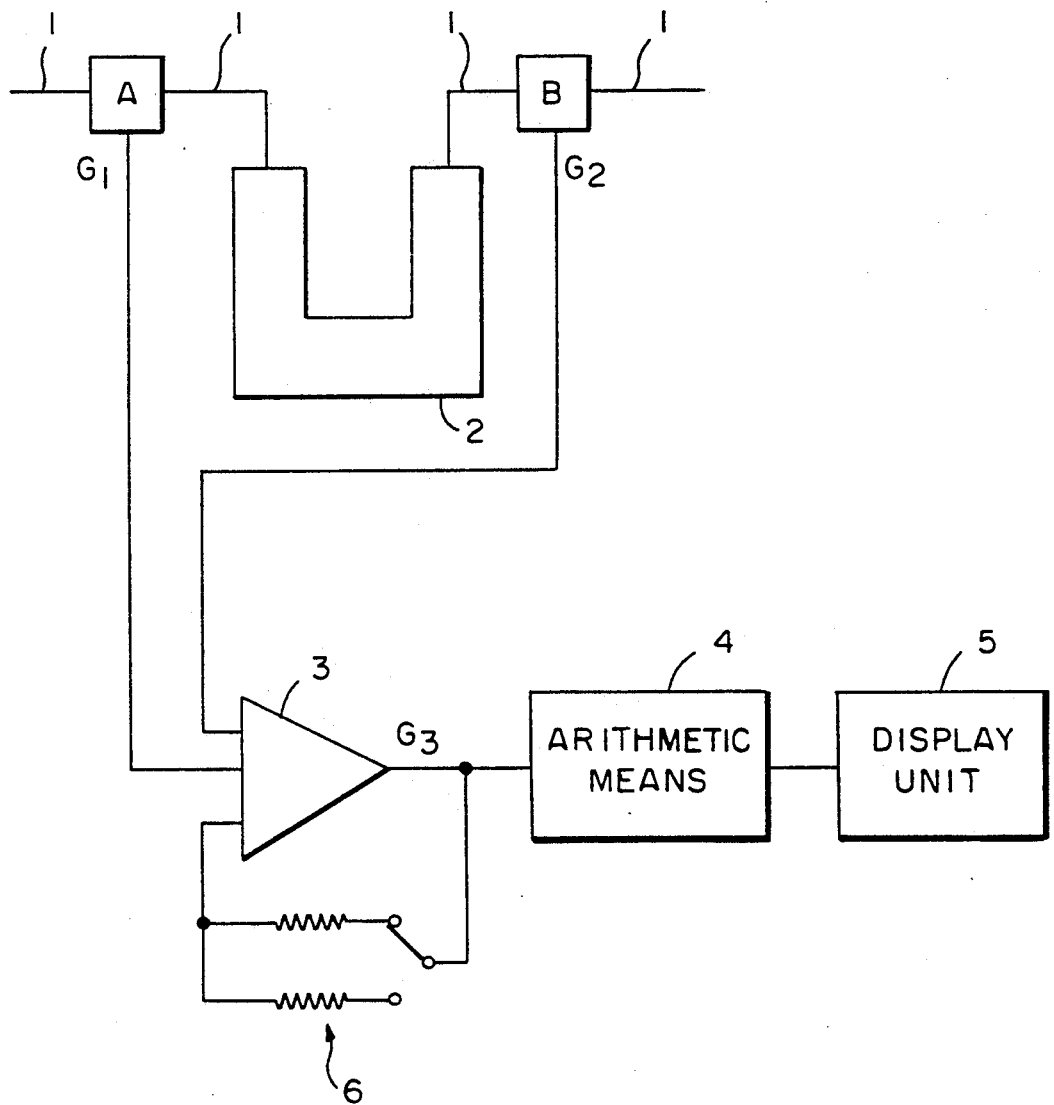
FIG. 4 is a circuit diagram showing a conventional device.
Figure 5:
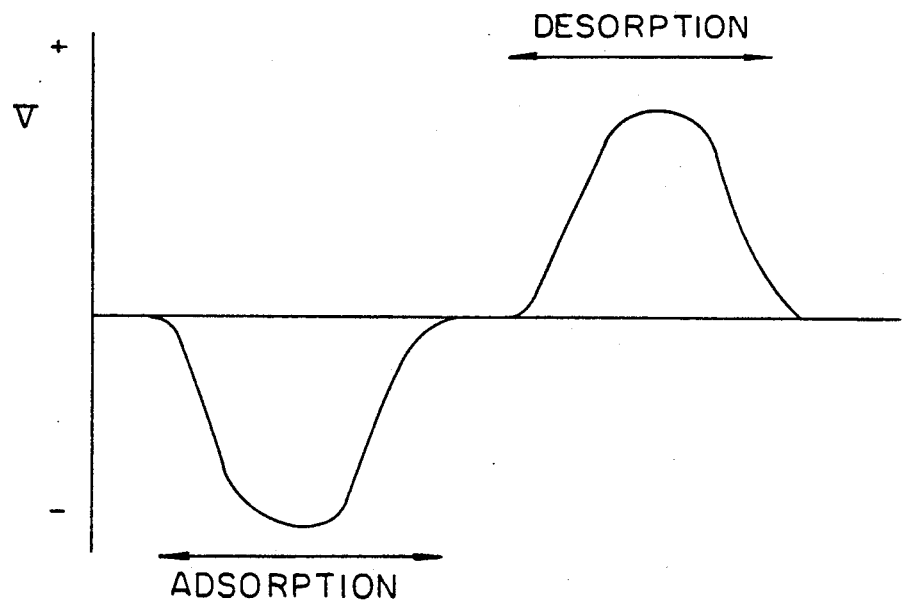
FIG. 5 is a graph showing a wave form indicating a state of signals generated from the amplifier when measuring gases are adsorbed on a sample in the sample cell and when the measuring gases adsorbed are desorbed.
Figure 6:
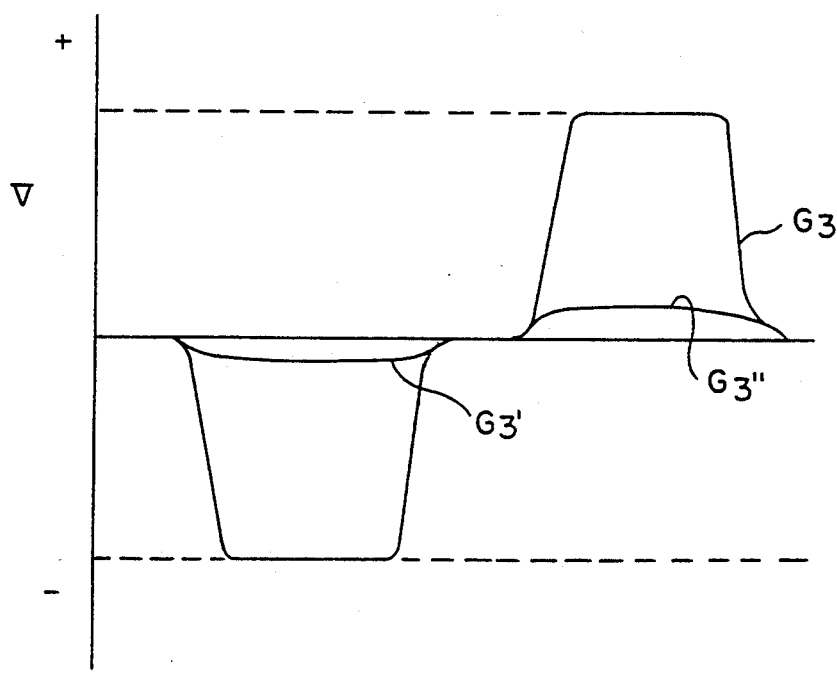
FIG. 6 is a graph showing a wave form indicating a signal to be outputted from the amplifier for a conventional device.

As shown in FIG. 3, the aforesaid output value determining circuit 12 comprises a circuit 12a for generating a signal for lowering the level of a gain, a circuit 12b for generating a signal for detecting a zero level, a circuit 12c for generating a signal for expanding the level of a gain, a first AND circuit 12d, a second AND circuit 12e, and an OR circuit 12f. The circuit 12a for generating the signal for lowering the level of the gain is so arranged as to receive the differential signal G3 to be outputted from the amplifier AMP, to compare the differential signal G3 with the set gain of the amplifier AMP, and to generate and output a signal GL for lowering the level of the gain when the differential signal G3 agrees with the set gain of the output of amplifier AMP. The circuit 12b for generating the signal for detecting the zero level is so arranged as to receive the differential signal G3, to detect the time at which the differential signal G3 turns from its negative value to zero, and to output a signal Go for detecting the zero level. The circuit 12c for generating the signal for expanding the level of the gain is so arranged as to receive the differential signal G3, to compare the differential signal G3 with a reference value predetermined with respect to the set gain, i.e., 50% of the set gain, and to detect that the differential signal G3 does not reach 50% of the set gain for a predetermined period of time, thereby outputting a signal GH for expanding the level of the gain. The first AND circuit 12d is to perform AND operation between the signal GL for lowering the level of the gain and the signal Go for detecting the zero level. The second AND circuit 12e is to perform AND operation between the signal GH for expanding the level of the gain and the signal Go for detecting the zero level. The OR circuit 12f is to perform OR operation between the signal outputted from the first AND circuit 12d and the signal outputted from the second AND circuit 12e.

The arithmetic unit 13 is so arranged as to calculate the surface area of a sample by integrating the differential signals G3 during the period of time for desorption of the gases, a differential signal being outputted from the amplifier AMP. The arithmetic unit 13 may be composed of a CPU.

The display unit 14 is a printer or a CRT unit for outputting or displaying data from the arithmetic unit 13.

Figure 2:
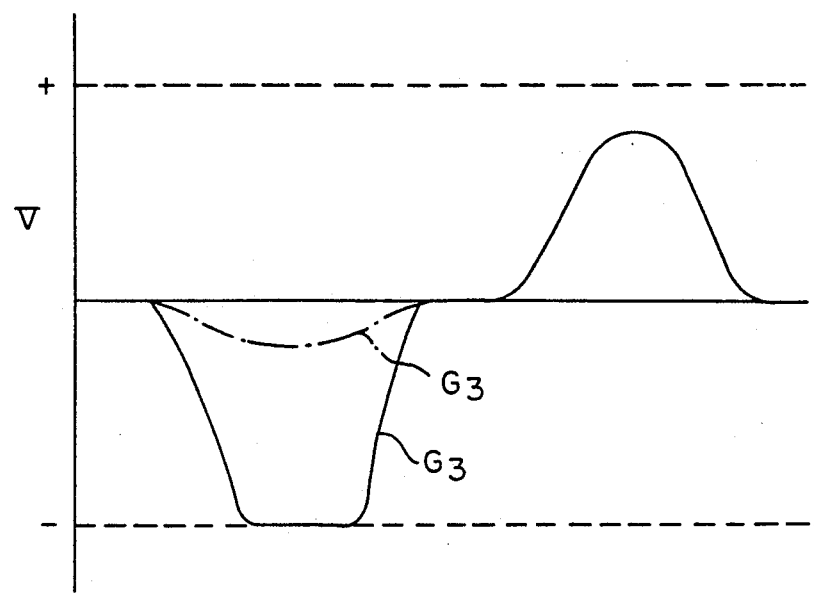
FIG. 2 is a graph showing a wave form indicating the action of the present invention.

When the measuring gases are adsorbed on the sample in the sample cell 11 in the device having the aforesaid structure, the differential signal G3 to be outputted from the amplifier AMP is a negative signal as shown in FIG. 2.

This negative signal is inputted into the output value determining circuit 12 which in turn is so arranged as to allow the negative differential signal G3 to be inputted into the circuit 12a for generating the signal G6 a lowering the level of the gain, the circuit 12b for generating the signal Go for detecting the zero level and the circuit 12c for generating the signal GH for expanding the level of the gain.

It is noted herein that, for instance, if the differential signal G3 is a signal which exceeds the gain, the signal GL for lowering the level of the gain is outputted from the circuit 12a for generating the signal for lowering the level of the gain. The signal GL for lowering (making more negative) the level of the gain is inputted into the first AND circuit 12d. On the other hand, the extent to which the measuring gases are adsorbed on the sample approaches its saturated state, the differential signal G3 to be outputted from the amplifier AMP increases from the negative value to the zero level and, as the measuring gases are adsorbed on the sample to a saturated extent, the differential signal G3 is turned to the zero level. At this time, the circuit 12b for generating the signal for detecting the zero level disposed in the output value determining circuit 12 detects the zero level to which the differential signal G3 has reached and generates the signal Go for detecting the zero level. The signal Go for detecting the zero level is outputted into the first AND circuit 12d which in turn outputs the signal GL for lowering the level of the gain through the OR circuit to the shift switch SW for shifting the gain of the amplifier AMP, in response to the signal Go for detecting the zero level, thereby lowering the gain of the amplifier AMP.

As a consequence, as shown in FIG. 2, the differential signal G3 to be outputted from the amplifier AMP can be outputted from the amplifier AMP without exceeding the set gain or cutoff limit L1 (dashed lines of FIG. 2) of the amplifier gain although the differential signal G3 would otherwise exceed the set gain if the gain would not be lowered. The differential signal G3 is then outputted and added up in the arithmetic unit 13, thereby operating to detect the amount of the gases adsorbed on the sample and generating the operation result into the display unit 14.

On the other hand, when the differential signal G3 to be outputted from the amplifier AMP is too small with respect to the set gain L1 as shown in FIG. 2, the signal GH for expanding the level of the gain is generated by the circuit 12c for generating the signal for expanding the level of the gain and it is outputted into the shift switch for shifting the level of the gain through the OR circuit by the second AND circuit 12e for inputting the signal GH for expanding the level of the gain and the signal Go for detecting the zero level, at the time when the period of time for adsorbing the gases is finished, thereby expanding the gain of the amplifier AMP.

As a result, as shown in FIG. 2, the differential signal G3 to be outputted from the amplifier AMP can be outputted as an appropriate output value from the amplifier AMP without exceeding the set gain L1 although the differential signal G3 would otherwise be considerably small during the period for desorption of the gases if the gain would not be expanded. The differential signal G3 is then outputted and added up in the arithmetic unit 13, thereby operating to detect the amount of the gases adsorbed on the sample and generating the operation result into the display unit 14.

As described hereinabove, the differential signal G3 during the period for desorption of the gases is adjusted appropriately by determining the output state of the differential signal G3 during the period for absorption of the gases, so that the device according to the embodiment of the present invention can always measure the amount of gases to an accurate extent.

FIELD OF INDUSTRIAL UTILIZATION

The system according to the Present invention can automatically adjust the gain so as for the signal outputted from the amplifier during the period for desorption of the gases not to exceed the set gain or cutoff value of the amplifier or to become too small with respect to the set gain or cutoff value of the amplifier by determining the state of the signal to be outputted from the amplifier during the period for adsorption of the gases. Hence, the surface area measuring device having the system for automatically shifting the measuring ranges can measure the surface area of the sample with accuracy, although the system is of a simple structure.

I claim:

1. In a surface area measuring device comprising:

a gas passage;

a sample cell mounted detachably in said gas passage;

said sample cell having a tube-like form containing a sample, a surface area of said sample to be measured for an amount of gases absorbed by said sample;

first measurement means, located in said gas passage and connected to a first end of said sample cell to which gases are supplied through said gas passage, for detecting a flow rate of gases to be supplied to said sample cell to measure an amount of supplied gases and generating a supply-gases-flow-rate detecting signal;

second measurement means, located in the gas passage and connected to a second end of said sample cell from which said supplied gases are discharged, for detecting a flow rate of gases discharged from said sample cell in order to measure an amount of discharge gases and generating a discharge-gases-flow-rate detecting signal;

an amplifier electrically connected to said first measurement means and to said second measurement means for receiving said supply-gases-flow-rate detecting signal and said discharge-gases-flow-rate detecting signal and amplifying a difference between said supply-gases-flow-rate detecting signal and said discharge-gases-flow-rate detecting signal, and generating a differential signal, said amplifier being capable of varying a gain;

arithmetic means, electrically connected to said amplifier to receive said differential signal, for calculating an amount of gases absorbed in said sample cell by integrating said differential signal;

an improvement of said measuring device comprising:

output value determining circuit electrical means, connected between said amplifier and said arithmetic means for receiving said differential signal to said amplifier and generating a shift signal for setting a gain of said amplifier to a low level when said differential signal reaches a set gain of an output of said amplifier and for generating a shift signal for setting a gain of said amplifier to a high level when said differential signal is smaller than a predetermined value with respect to said set gain during a period of time that gases absorbed in a sample are desorbed; and shift switch means electrically connected with said output value determining circuit means and said amplifier, for receiving said shift signal and switching said gain of said amplifier in accordance with said shift signal.

2. A surface area measuring device according to claim 1 wherein said output value determining circuit means comprises:

first circuit means for generating a preset digital signal for lowering a level of said gain, said first circuit means electrically connected with said amplifier, for receiving said differential signal generated from said amplifier, for comparing said differential signal with said set gain, and for outputting said preset digital signal when said differential signal agrees with said set gain;

second circuit means for generating a digital zero level detecting signal, said second circuit means electrically connected with said amplifier for receiving said differential signal, for detecting a time at which said differential signal turns from a negative value to zero, and for outputting a digital zero level detecting signal;

third circuit means for generating a preset digital signal for expanding a level of said gain, said second circuit means electrically connected with said amplifier, for receiving said differential signal, for comparing said differential signal with a value predetermined with respect to said set gain, and for detecting whether said differential signal does not reach said value for a predetermined period of time, thereby outputting said preset digital signal;

first AND circuit means, electrically connected with said first circuit means and said second circuit means for receiving said digital signal for lowering said level of said gain and said digital zero level detecting signal, for performing AND operation between said digital signal for lowering said level of said gain and said digital zero level detecting signal and outputting a digital signal;

second AND circuit means, electrically connected with said third circuit means and said second circuit means, for receiving said digital signal for expanding said level of said gain and said digital zero level detecting signal, for performing AND operation between said digital signal for expanding said level of said gain and said digital zero level detecting signal and outputting a digital signal; and OR circuit means, electrically connected with said first AND circuit means and said second AND circuit means, for receiving said digital signal outputted form said first AND circuit means and said digital signal outputted from said second AND circuit means, for performing OR operation between said digital signal outputted from said first AND circuit means and said digital signal outputted from said second AND circuit means and outputting a shifting signal.

* * * * *